United States Patent
Taft et al.

(10) Patent No.: US 12,083,299 B2
(45) Date of Patent: *Sep. 10, 2024

(54) RIVET SHUNT AND METHOD OF DEPLOYMENT

(71) Applicant: NXT Biomedical, LLC, Irvine, CA (US)

(72) Inventors: Robert C. Taft, Orange, CA (US); Glen Rabito, Lake Forest, CA (US); Robert S. Schwartz, Inver Grove Heights, MN (US)

(73) Assignee: NXT Biomedical, LLC, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/365,897

(22) Filed: Aug. 4, 2023

(65) Prior Publication Data

US 2023/0372684 A1  Nov. 23, 2023

Related U.S. Application Data

(63) Continuation of application No. 16/785,501, filed on Feb. 7, 2020, now Pat. No. 11,752,314.

(Continued)

(51) Int. Cl.
*A61M 27/00* (2006.01)
*A61F 2/06* (2013.01)
(Continued)

(52) U.S. Cl.
CPC .............. *A61M 27/002* (2013.01); *A61F 2/06* (2013.01); *A61F 2/958* (2013.01); *A61F 2002/91525* (2013.01)

(58) Field of Classification Search
CPC .. A61F 2002/91508; A61F 2002/91525; A61F 2/82; A61F 2/958; A61F 2/04;
(Continued)

(56) References Cited

U.S. PATENT DOCUMENTS 5,584,803 A  12/1996 Stevens
5,895,404 A  4/1999 Ruiz
(Continued)

FOREIGN PATENT DOCUMENTS

EP  1029517 A2  8/2000
JP  2002-524196 A  8/2002
(Continued)

OTHER PUBLICATIONS

Bhamra-Ariza, Paul MBBS, MD, *Percutaneous Interventional Therapies for the Treatment of Patients With Severe Pulmonary Hypertension*, vol. 63, No. 7, Journal of the American College of Cardiology, Published by Elsevier Inc., 2014, pp. 611-618.
(Continued)

*Primary Examiner* — Rebecca E Eisenberg
*Assistant Examiner* — Linnae E. Raymond
(74) *Attorney, Agent, or Firm* — Inskeep IP Group, Inc.

(57) ABSTRACT

A shunt is described that expands to an hourglass shape. As the shunt expands, both of its ends radially flare outwards relative to its middle section and the length of the shunt foreshortens, which causes the flared ends to engage the tissue surrounding a puncture or aperture within a patient's tissue.

19 Claims, 12 Drawing Sheets

Related U.S. Application Data

(60) Provisional application No. 62/942,631, filed on Dec. 2, 2019, provisional application No. 62/896,144, filed on Sep. 5, 2019, provisional application No. 62/802,656, filed on Feb. 7, 2019.

(51) Int. Cl.
*A61F 2/915* (2013.01)
*A61F 2/958* (2013.01)

(58) Field of Classification Search
CPC .... A61F 2/06; A61F 2/07; A61F 2/844; A61F 2/86; A61B 17/11; A61B 17/1107; A61B 17/1114; A61B 17/0057; A61B 2017/1107; A61B 2017/1121; A61B 2017/00575–00641
See application file for complete search history.

(56) References Cited

U.S. PATENT DOCUMENTS

| | | |
|---|---|---|
| 6,214,029 B1 | 4/2001 | Thill et al. |
| 6,344,022 B1 | 2/2002 | Jarvik |
| 6,395,212 B1 | 5/2002 | Solem |
| 6,669,708 B1 | 12/2003 | Nissenbaum |
| 6,935,344 B1 | 8/2005 | Aboul-Hosn |
| 7,022,131 B1 | 4/2006 | Derowe et al. |
| 7,628,768 B2 | 12/2009 | Faul et al. |
| 7,828,814 B2 | 11/2010 | Brenneman et al. |
| 7,967,769 B2 | 6/2011 | Faul et al. |
| 8,034,063 B2 | 10/2011 | Binmoeller |
| 8,048,016 B2 | 11/2011 | Faul et al. |
| 8,088,171 B2 | 1/2012 | Brenneman |
| 8,172,896 B2 | 5/2012 | McNamara et al. |
| 8,226,592 B2 | 7/2012 | Brenneman et al. |
| 8,236,014 B2 | 8/2012 | Brenneman et al. |
| 8,273,095 B2 | 9/2012 | Brenneman et al. |
| 8,382,697 B2 | 2/2013 | Brenneman et al. |
| 8,425,539 B2 | 4/2013 | Binmoeller et al. |
| 8,454,632 B2 | 6/2013 | Binmoeller et al. |
| 8,460,372 B2 | 6/2013 | McNamara et al. |
| 8,523,800 B2 | 9/2013 | Brenneman et al. |
| 8,617,196 B2 | 12/2013 | Binmoeller |
| 8,641,724 B2 | 2/2014 | Brenneman et al. |
| 8,641,747 B2 | 2/2014 | Brenneman et al. |
| 8,734,472 B2 | 5/2014 | Brenneman et al. |
| 8,740,962 B2 | 6/2014 | Finch et al. |
| 8,777,967 B2 | 7/2014 | Binmoeller |
| 8,784,437 B2 | 7/2014 | Binmoeller |
| 8,882,697 B2 | 11/2014 | Celermajer et al. |
| 8,926,545 B2 | 1/2015 | Brenneman et al. |
| 8,932,341 B2 | 1/2015 | Brenneman |
| 8,951,223 B2 | 2/2015 | McNamara et al. |
| 9,005,155 B2 | 4/2015 | Sugimoto |
| 9,023,097 B2 | 5/2015 | Brenneman et al. |
| 9,023,100 B2 | 5/2015 | Quadri et al. |
| 9,232,997 B2 | 1/2016 | Sugimoto et al. |
| 9,277,995 B2 | 3/2016 | Celermajer et al. |
| 9,364,259 B2 | 6/2016 | Lunsford et al. |
| 9,381,041 B2 | 7/2016 | Brown et al. |
| 9,468,441 B2 | 10/2016 | Brenneman |
| 9,510,832 B2 | 12/2016 | Brenneman |
| 9,550,022 B2 | 1/2017 | Brenneman et al. |
| 9,649,480 B2 | 5/2017 | Sugimoto et al. |
| 9,706,997 B2 | 7/2017 | Brenneman |
| 9,757,107 B2 | 9/2017 | McNamara et al. |
| 9,775,636 B2 | 10/2017 | Fazio et al. |
| 9,833,347 B2 | 12/2017 | Christakis et al. |
| 9,888,926 B2 | 2/2018 | Phan et al. |
| 10,052,106 B2 | 8/2018 | Binmoeller et al. |
| 10,076,330 B2 | 9/2018 | Sander et al. |
| 10,098,643 B2 | 10/2018 | Brenneman |
| 10,111,998 B2 | 10/2018 | Brenneman et al. |
| 10,207,087 B2 | 2/2019 | Keren et al. |
| 10,390,833 B2 | 8/2019 | Sander et al. |
| 2002/0128587 A1 | 9/2002 | Aboul-Hosn |
| 2002/0169494 A1 | 11/2002 | Mertens et al. |
| 2003/0040736 A1 | 2/2003 | Stevens |
| 2003/0187322 A1 | 10/2003 | Siess |
| 2004/0093067 A1 | 5/2004 | Srael |
| 2005/0228413 A1 | 10/2005 | Binmoeller et al. |
| 2006/0116625 A1 | 6/2006 | Renati et al. |
| 2006/0259074 A1 | 11/2006 | Kelleher et al. |
| 2009/0281557 A1 | 11/2009 | Sander et al. |
| 2010/0004728 A1* | 1/2010 | Rao ............... A61F 2/91 623/1.11 |
| 2010/0179643 A1 | 7/2010 | Shalev |
| 2010/0198013 A1 | 8/2010 | Binmoeller |
| 2010/0222869 A1 | 9/2010 | Delaney |
| 2010/0268029 A1 | 10/2010 | Phan et al. |
| 2011/0137394 A1 | 6/2011 | Lunsford et al. |
| 2011/0218479 A1 | 9/2011 | Rottenberg et al. |
| 2011/0257462 A1 | 10/2011 | Rodefeld |
| 2012/0109277 A1 | 5/2012 | Lepulu et al. |
| 2012/0130417 A1 | 5/2012 | Lepulu et al. |
| 2012/0303112 A1 | 11/2012 | Armstrong et al. |
| 2013/0030521 A1 | 1/2013 | Nitzan |
| 2013/0178783 A1 | 7/2013 | McNamara et al. |
| 2013/0178784 A1 | 7/2013 | McNamara et al. |
| 2014/0025164 A1 | 1/2014 | Montorfano et al. |
| 2014/0343348 A1 | 11/2014 | Kaplan et al. |
| 2015/0057687 A1 | 2/2015 | Gittard |
| 2015/0081006 A1 | 3/2015 | Chuter et al. |
| 2015/0313598 A1 | 11/2015 | Todd et al. |
| 2016/0120550 A1 | 5/2016 | McNamara et al. |
| 2016/0135941 A1 | 5/2016 | Binmoeller et al. |
| 2017/0035427 A1 | 2/2017 | Sander et al. |
| 2017/0071722 A1 | 3/2017 | Rafiee |
| 2018/0110634 A1 | 4/2018 | Giasolli et al. |
| 2018/0221632 A1 | 8/2018 | Scheule et al. |
| 2018/0289463 A1 | 10/2018 | Binmoeller et al. |
| 2018/0353184 A1 | 12/2018 | Sander et al. |
| 2019/0008628 A1 | 1/2019 | Eigler et al. |
| 2019/0099589 A1 | 4/2019 | Walsh et al. |
| 2019/0247051 A1 | 8/2019 | Siddiqui |
| 2020/0306432 A1 | 10/2020 | Pekkan |

FOREIGN PATENT DOCUMENTS

| | | | |
|---|---|---|---|
| JP | 2010-524585 A | 7/2010 | |
| JP | 2017-517309 A | 6/2017 | |
| WO | WO 2000/015147 A1 | 3/2000 | |
| WO | WO 2005/020848 A2 | 3/2005 | |
| WO | WO-2007051183 A1 * | 5/2007 | ............... A61F 2/91 |
| WO | WO 2008/131266 A1 | 10/2008 | |
| WO | WO 2012/143731 A1 | 10/2012 | |
| WO | WO 2015/168508 A2 | 11/2015 | |
| WO | WO 2019/006332 A1 | 1/2019 | |

OTHER PUBLICATIONS

WIPO, U.S. International Search Authority, International Search Report and Written Opinion mailed May 4, 2020 in International Patent Application No. PCT/US2020/0017361, 11 pages.

European Patent Office, Extended European Search Report dated Jan. 30, 2023 in European Patent Application No. 20752698.9, 12 pages.

China Patent Office, Office Action dated Jul. 28, 2022 with English translation in Chinese Patent Application No. 201980073629.X, 13 pages.

WIPO, U.S. International Search Authority, International Search Report and Written Opinion mailed Dec. 6, 2019 in International Patent Application No. PCT/US2019/052025, 10 pages.

Japanese Patent Office, Office Action dated Oct. 3, 2023 with English translation in Japanese Patent Application No. 2021-545895, 9 pages.

Japanese Patent Office, Final Office Action dated Apr. 2, 2024 with English translation in Japanese Patent Application No. 2021-545895, 7 pages.

(56) References Cited

OTHER PUBLICATIONS

CNIPA, Office Action dated Jun. 8, 2024 with English translation in Chinese Patent Application No. 202080027031.X, 11 pages.

* cited by examiner

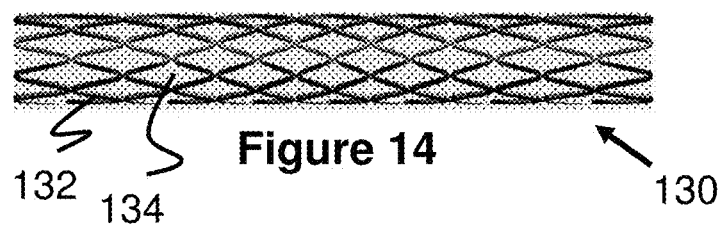
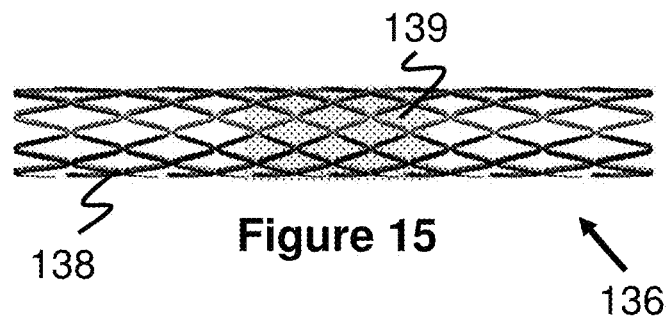
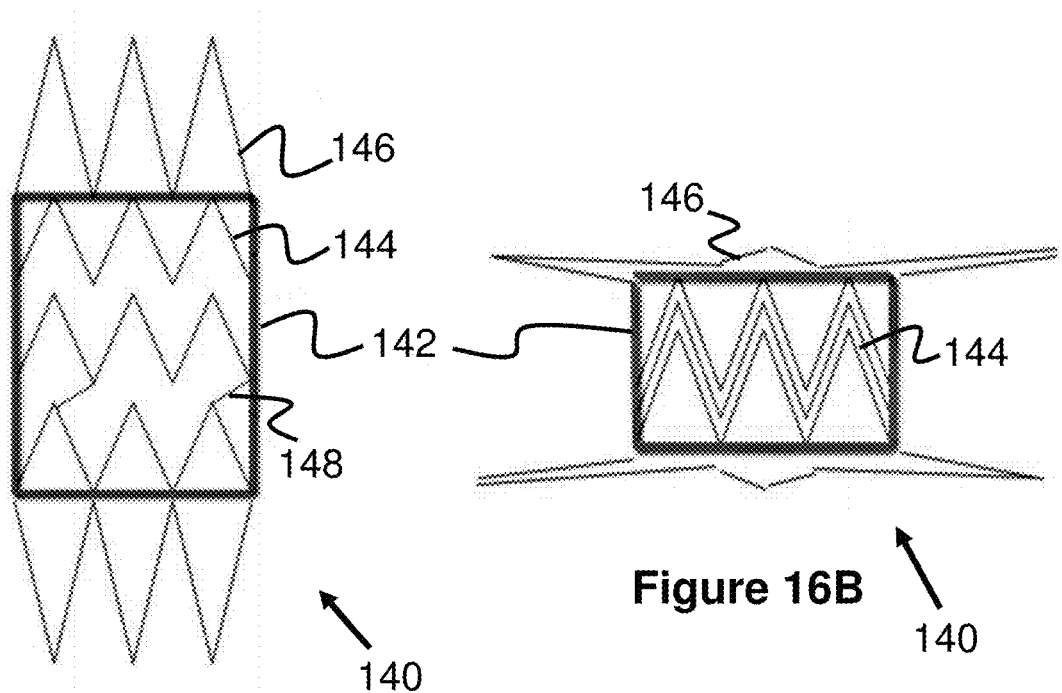

RIVET SHUNT AND METHOD OF DEPLOYMENT

RELATED APPLICATIONS

This application is a continuation of U.S. patent application Ser. No. 16/785,501 entitled Rivet Shunt And Method Of Deployment, which claims benefit of and priority to U.S. Provisional Application Ser. No. 62/802,656 filed Feb. 7, 2019 entitled Method and Technology for Creating Connections and Shunts Between Vessels and Chambers of Biological Structures, U.S. Provisional Application Ser. No. 62/896,144 filed Sep. 5, 2019 entitled Rivet Stent, and U.S. Provisional Application Ser. No. 62/942,631 filed Dec. 2, 2019 entitled Resizable Rivet Stent, all of which are hereby incorporated herein by reference in their entireties.

BACKGROUND OF THE INVENTION

An artificial shunt serves as a hole or small passage that allows movement of fluid from one part of a patient's body to another, or, more specifically, from one body lumen to another body lumen. Such body lumens can be associated with virtually any organ in the body but are most commonly associated with lumens in the heart, lungs, cranium and the liver.

Shunts can be used to treat many different conditions. Such conditions include, but are not limited to, pulmonary hypertension, heart failure, hypertension, kidney failure, volume overload, hypertrophic cardiomyopathy, valve regurgitation, and numerous congenital diseases.

Numerous prior art shunt designs exist as exemplified by U.S. Pat. No. 9,510,832, the contents of which is hereby incorporated by reference. As is appreciated by one of skill in the art, the efficacy and safety of a shunt in its intended application largely depends on such attributes as precise shunt placement, secure shunt fixation, shunt durability, minimization of regions of possible fluid stasis, ease of deployment, and adjustability over time, to name a few.

As such, there is a need to constantly improve and refine prior art shunt designs to arrive at a shunt that effectively and safely treats multiple conditions while at the same time allows for ease of use and reduced costs.

SUMMARY OF THE INVENTION

In one embodiment, the present invention is directed to a shunt that expands to an hourglass shape. As the shunt expands, both of its ends radially flare outwards relative to its middle section. Additionally, the length of the shunt foreshortens which causes the flared ends to engage the tissue surrounding a puncture or aperture within a patient's tissue, not unlike a rivet. In an alternate embodiment, only one of its ends radially flares outwards relative to its middle section, while the opposite end maintains a diameter similar to its middle section.

In one embodiment, the shunt achieves this shape by having a laser-cut body that forms a plurality of cells. The cells near the middle of the shunt have a smaller size (e.g., length, width) than the remaining cells. The cells near both the proximal and distal ends of the shunt have a larger size (e.g., length, width) than the middle cells, causing them to radially expand to a greater diameter. Further, as the cells radially expand, they increase in width, which causes their length to decrease. The decreased cell length causes the shunt, as a whole, to foreshorten or decrease in length.

In one embodiment, the shunt can be deployed with a balloon catheter. The shunt is compressed over the balloon catheter and, when inflated, causes the shunt to expand.

In one embodiment, the balloon catheter has a balloon that inflates to an hourglass shape. In other words, the balloon's proximal and distal regions expand to a larger diameter relative to the middle portion.

In one example method of the present invention, a distal end of a balloon catheter has a shunt disposed over its balloon. The shunt and balloon are positioned about halfway through an opening in a patient's tissue. The balloon is inflated to an hourglass shape, causing the shunt to similarly expand to an hourglass shape while also foreshortening. The flared ends of the shunt are thereby caused to engage the tissue surrounding the opening.

The prior method can further include a later, secondary expansion of the shunt to further increase its diameter. This can be achieved by advancing a second balloon catheter into the shunt and expanding its balloon to a desired shunt passage diameter.

In another embodiment of the present invention, the shunt includes barbs, hooks or similar anchoring mechanisms on its outer surface.

In another embodiment of the present invention, the shunt may include a cover located either along its entire length or along only a portion of its length (e.g., a middle portion).

In another embodiment, the balloon delivery catheter may include positioning devices that provide a tactile resistance to indicate the shunt is aligned at a desired position. For example, the positioning device may include a plurality of arms extending from the catheter body, an annular ring positioned on the outer surface of the shunt, or portions of the shunt that are heat-set to radially expand.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIG. 14 illustrates a side view of another embodiment of a shunt according to the present invention.

FIG. 15 illustrates a side view of another embodiment of a shunt according to the present invention.

FIG. 16A illustrates a side view of another embodiment of a shunt according to the present invention.

FIG. 16B illustrates a side view of the shunt of FIG. 16A.

DESCRIPTION OF EMBODIMENTS

Figure 1A:
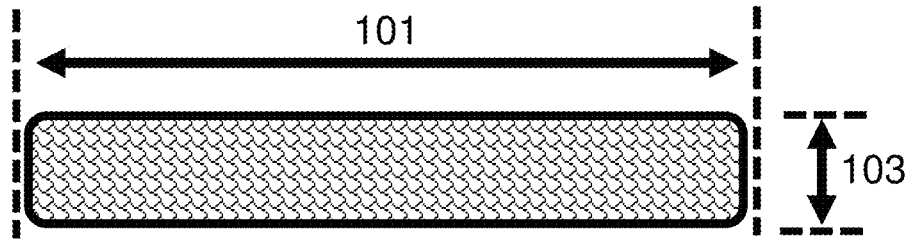
FIG. 1A is an illustration of a shunt in a compressed configuration according to the present invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The present invention is generally directed to a shunt and a method of deploying a shunt. More specifically, the shunt radially expands to an hourglass or rivet shape while also longitudinally foreshortening. The shunt is initially positioned within a tissue opening and then expanded, which causes the distal and proximal ends of the shunt to flare radially outwards and move towards each other. When fully expanded, these radially flared ends engage the tissue surrounding the opening, creating a smooth transition between either side of the tissue.

This shunt design provides several advantages over prior shunt designs. For example, the shunt may "self-position" itself within the tissue opening due to its flared shape and therefore provides increased precision in its positioning than prior designs. The flared portions also provide strong attachment to the surrounding tissue as compared with prior shunt designs. Finally, the shunt may have a small collapsed profile and yet can expand to a consistent inner diameter with high radial force. This allows the use of low-profile balloons to assist in the expansion of the shunt to achieve consistent and reliable implantation results.

A stent design that can be modified for use as a shunt in accordance with the principles of the present invention as explained herein is disclosed in U.S. Pat. No. 6,068,656 to Oepen, the entire contents of which is incorporated herein by reference.

As discussed in greater detail in this specification, the foreshortening and hourglass shape can be achieved in several different ways and the shunts themselves may have several different features. It should be explicitly understood that the features shown in the different embodiments of this specification can be interchangeably used with features of other embodiments in this specification. In other words, it is intended that the features of the embodiments can be "mixed and matched" with each other.

Figure 1B:
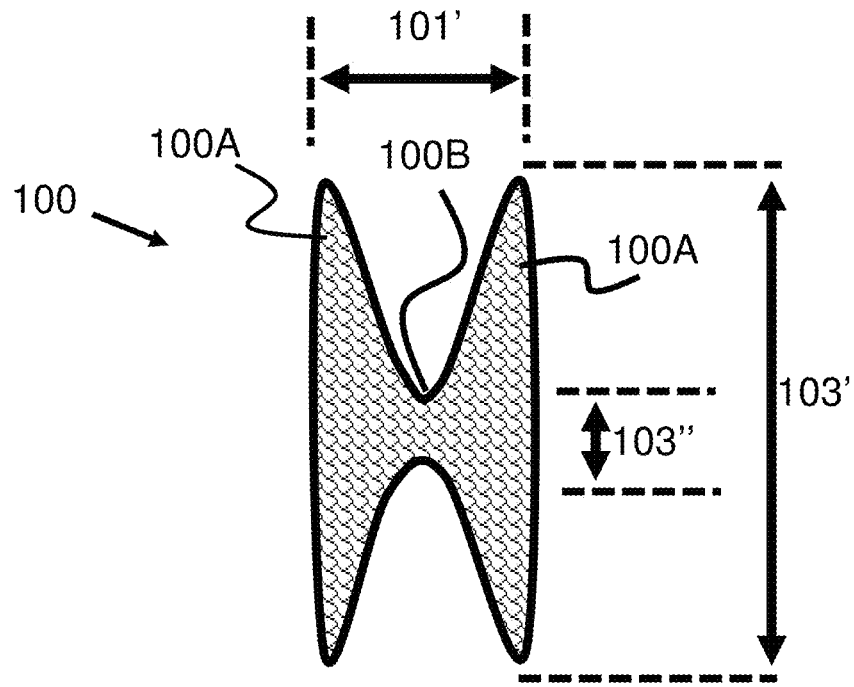
FIG. 1B is an illustration of the shunt of FIG. 1A in a radially expanded position.

FIGS. 1A and 1B illustrate the change in shape of one embodiment of a tubular shunt 100 of the present invention. In FIG. 1A, the shunt 100 is shown in a radially compressed configuration having a relatively long length 101 and a relatively small, uniform diameter 103. As the shunt 100 is deployed, its length substantially decreases to 101' and its diameter increases. More specifically, end portions 100A increase to a maximum radial diameter of 103' and then decrease in diameter towards a middle region 100B, which has a diameter of 103".

In one example, when compressed, the shunt 100 has a length 101 of about 20 mm and a diameter 103 of about 1.5 mm, and when expanded the shunt 100 has a diameter 103' of the end portions 100A of about 8 mm and a diameter 103" of the middle region 100B of about 5 mm.

In another example, when compressed, the shunt 100 has a length 101 of about 30 mm and a diameter 103 of about 2.2 mm, and when expanded the shunt 100 has a diameter 103' of the end portion 100A of about 8 mm and a diameter 103" of the middle region 100B of about 4 mm.

In another example, when compressed, the shunt 100 has a length 101 of about 22 mm and a diameter 103 of about 3.5 mm, and when expanded the shunt 100 has a diameter 103' of the end portion 100A of about 24 mm and a diameter 103" of the middle region 100B of about 20 mm.

Figure 2:
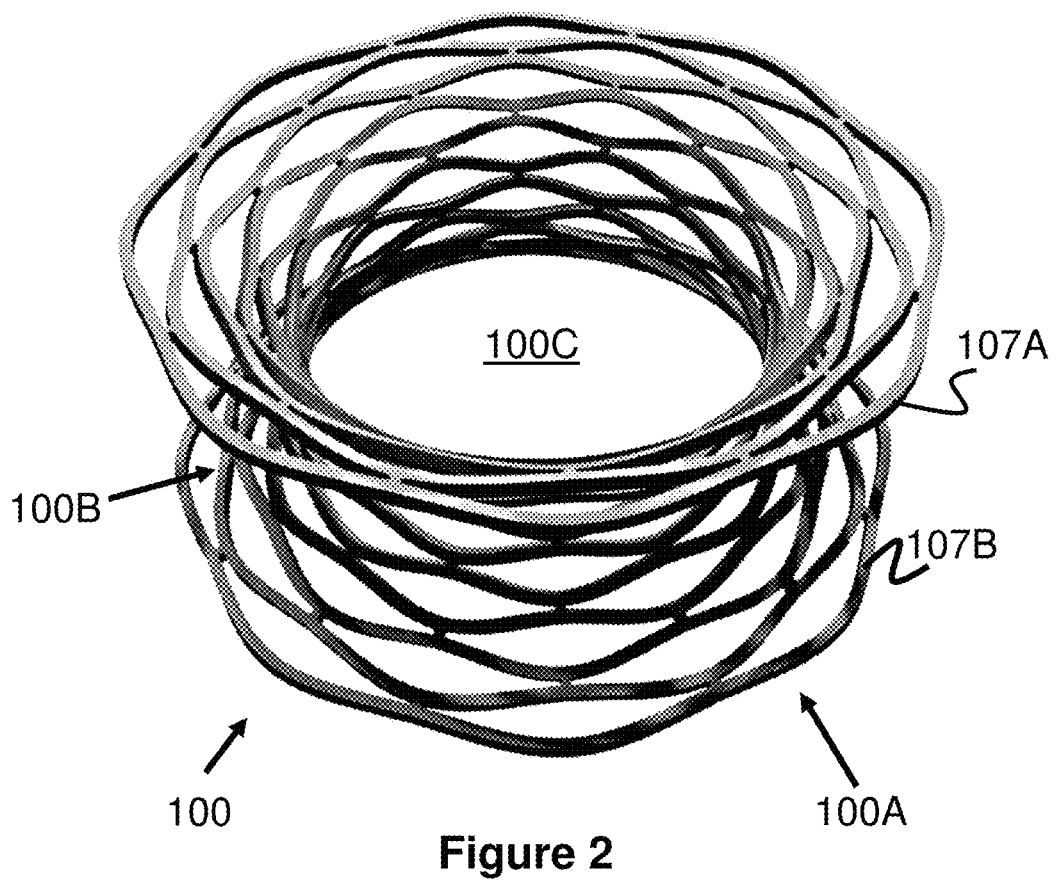
FIG. 2 is a perspective view of the shunt of FIG. 1A in a radially expanded position.
Figure 3:
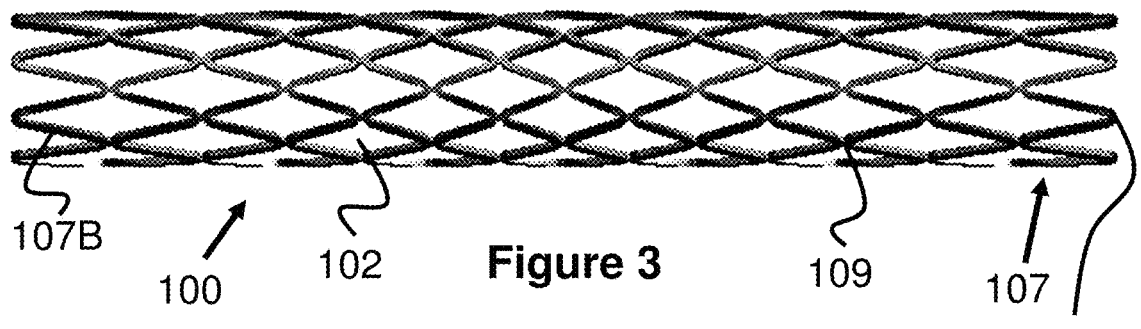
FIG. 3 is a side view of the shunt of FIG. 1A in a compressed configuration.
Figure 4A:
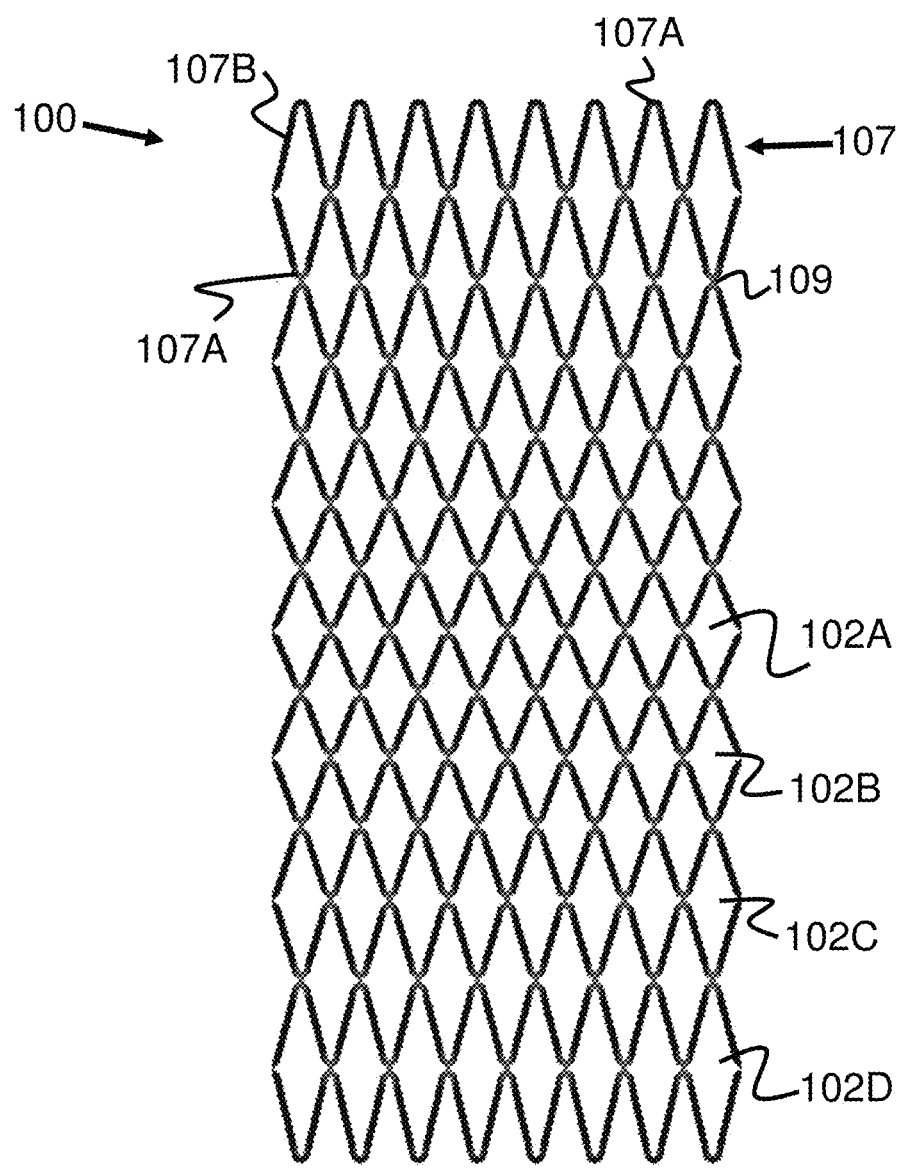
FIG. 4A is a top view of the cell pattern of the shunt of FIG. 1A.

As seen in FIGS. 2-4, this embodiment of the shunt 100 includes a plurality of tubular radial bands 107 that are each formed from a plurality of uniform, alternating waves that create the shunt passage 100C. Put another way, and referring particularly to FIGS. 3 and 4A, each radial band 107 comprises a plurality of straight regions 107B joined together to create a pattern of triangular peaks 107A that alternate their longitudinal directions. The peaks 107A of each radial band 107 are aligned with each other and connected via a small, straight portion 109, which effectively creates diamond-shaped cells 102 when radially compressed. As a result of this design, the angle of each peak 107A increases as the shunt 100 is radially expanded and the radial bands 107 become closer together to each other, which causes longitudinal foreshortening (i.e., a decrease in length of the shunt 100).

Figure 4B:
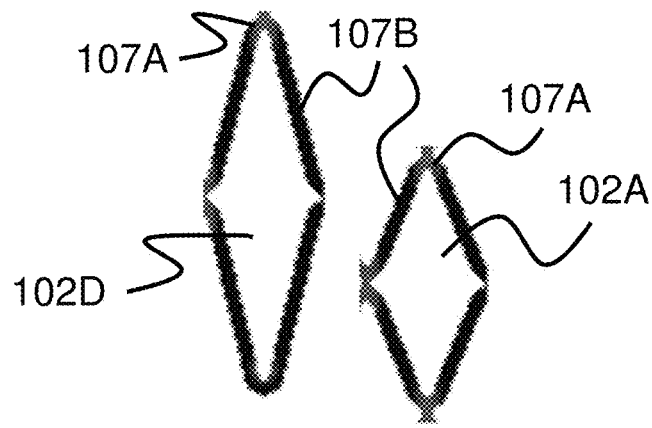
FIG. 4B is a top view of two cells from the cell pattern in FIG. 4A.

One mechanism for causing the radial flaring of the ends 100A of the shunt 100 can be seen in FIGS. 4A and 4B, which illustrate the pattern of the shunt 100 as if it were longitudinally cut and flattened. Specifically, a pattern of cells 102 can be created in which some cells 102A, 102B, 102C, 102D are longer in their proximal-to-distal length than other cells (i.e., they have longer straight regions 107B). Preferably, cells 102 in the middle of the shunt 100 have the smallest length and each row of cells 102 progressively increase in length the further away from the middle they are. Alternately, larger length cells 102 can be located only near the ends of the shunt 100.

For example, middle cell 102A has a first length; longitudinally adjacent cell 102B has a second, longer length than cell 102A; longitudinally adjacent cell 102C has a third, longer length than cell 102B; and longitudinally adjacent cell 102D has a fourth, longer length than cell 102C.

To better see this distinction, FIG. 4B comparatively illustrates cells 102A and 102D next to each other. In a compressed configuration, the larger cell 102D will have longer straight portions 107B and a smaller angle of peak 107A relative to cell 102A. However, when expanding, the larger straight portions 107B allow those cells to expand to a larger diameter and foreshorten more than cell 102A. In this manner, the expanded shape and amount of foreshortening can be determined.

The size and ratio of the cells 102 and straight portions 107B can vary, depending on the desired expanded shape of the shunt 100. For example, having dramatically larger end cells (e.g., cells 102C and 102D) may cause the expanded configuration of the shunt 100 to have a larger flare diameter size relative to its middle portion. In one specific example, the size increases of the straight portion 107B (i.e., struts) of each radial band 107 can be seen in the following listing, which begins with the straight portion 107B in the middle cell 102A and progresses towards the end of the shunt 100. For a shunt with flaring on both ends, the progression of size increase would be the same on either side of the center region of the shunt. It will be appreciated that through creative configurations of the size progression described herein, one flare could be a different size or configuration from its opposite flare and thus the shunt can be specifically tailored to the particular use and location in the patient's body. Note, this specific example illustrates a greater number of straight portions 107B and therefore cells 102 than that shown in FIG. 4A. However, the shunt 100 may include a variety of different cell numbers. Straight portion 107B example sizes: 1.218 mm, 1.242 mm, 1.287 mm, 1.351 mm, 1.432 mm, 1.528 mm, 1.638 mm, 1.763 mm, 1.897 mm, 2.036 mm.

In addition to the variable size of the cells 102 along the length of the shunt 100, the shunt 100 can be heat set to an hourglass shape when unconstrained to provide additional expansion force, either with or without the assistance of a balloon catheter.

Notwithstanding the above cell design, it is noted that multiple cell variations are contemplated in accordance with the present invention. In this regard, a key design parameter is that each "row" or band in the shunt body reaches maximum expansion at a particular diameter to achieve the final desired shape.

Figure 5:
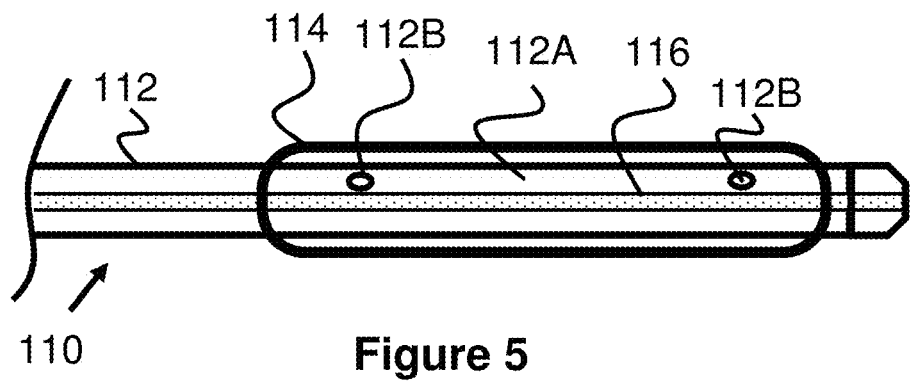
FIG. 5 illustrates a balloon catheter in a deflated configuration according to the present invention.
Figure 6:
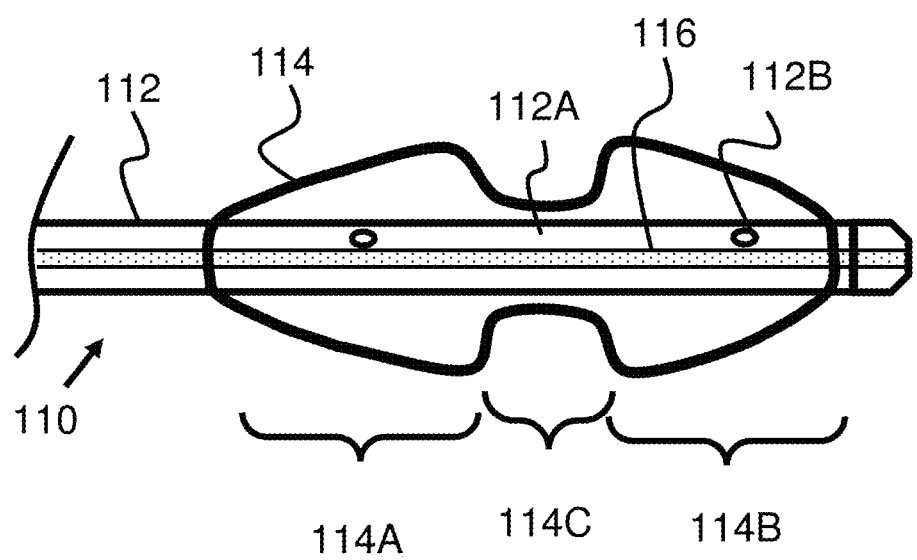
FIG. 6 illustrates the balloon catheter of FIG. 5 in an expanded configuration according to the present invention.

The shunt 100 can be delivered and expanded via a balloon catheter 110, as seen in FIGS. 5 and 6. In one embodiment, a balloon 114 is disposed on its distal end of a tubular catheter body 112. The interior of the catheter body 112 has an inflation lumen 112A that opens to proximal and distal inflation ports 112B within the balloon 114. A guidewire lumen 116 is located within the catheter body 112, opening on the proximal and distal ends of the body 112.

As seen in FIG. 6, the balloon 114 may inflate to an hourglass shape that has a smaller diameter middle region 114C than the proximal region 114A and distal region 114B of the balloon 114. There are several different techniques to achieve this inflated shape of the balloon 114. For example, the balloon 114 can be composed of a compliant material and a non-compliant band (not shown) can be positioned around the middle region 114C. In another example, the proximal region 114A and distal region 114B can be composed of a material with different expansion properties than the middle region 114C (e.g., a compliant middle region with noncompliant proximal/distal regions, or a noncompliant middle region with compliant proximal/distal regions).

Figure 7:
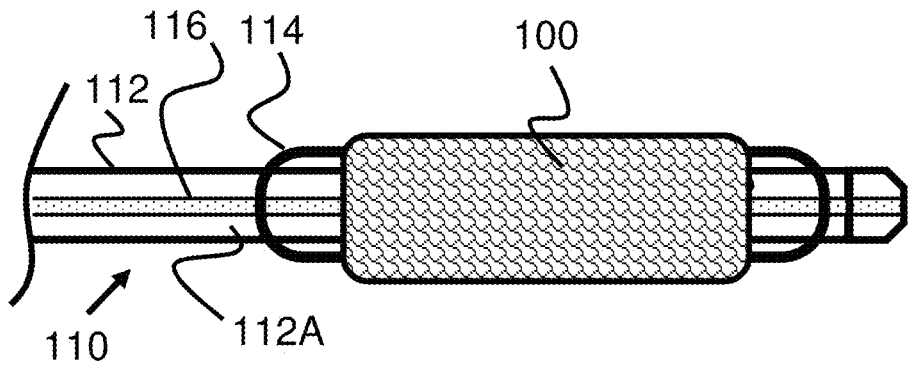
FIG. 7 illustrates the balloon catheter of FIG. 5 with a shunt compressed over it according to the present invention.
Figure 8:
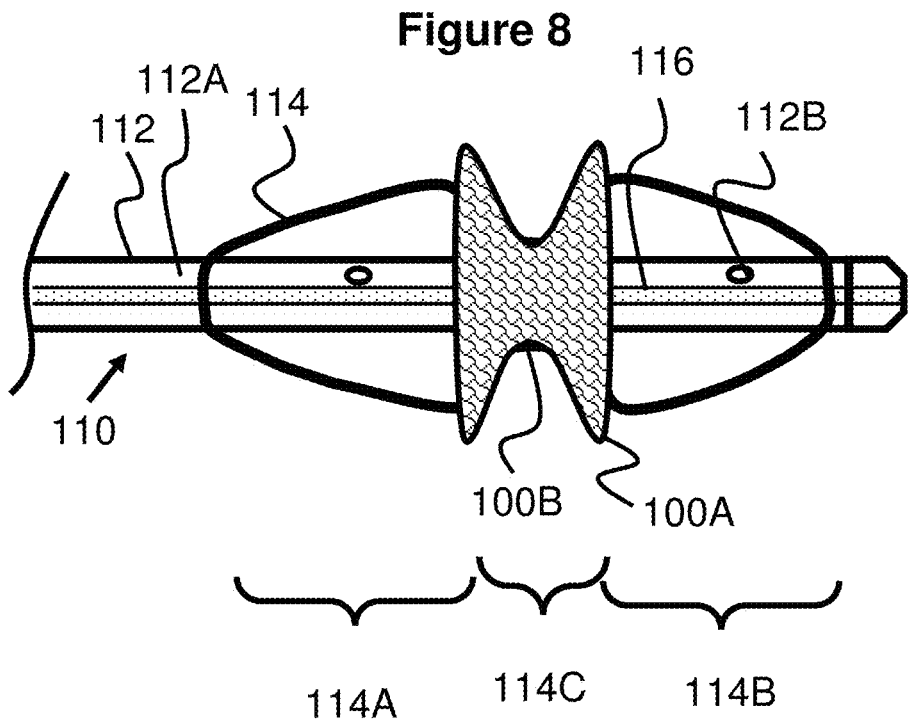
FIG. 8 illustrates the balloon catheter of FIG. 6 with a shunt in its expanded position according to the present invention.

FIGS. 7 and 8 illustrate the shunt 100 positioned over the balloon 114. Preferably, the shunt 100 is loaded onto the balloon 114 so that the middle region 100B of the shunt 100 is aligned with the middle region 114C of the balloon 114. In that regard, as the balloon 114 expands, the proximal region 114A and distal region 114B cause the end regions 100A of the shunt 100 to expand to a larger diameter than the middle region 100B.

Figure 9:
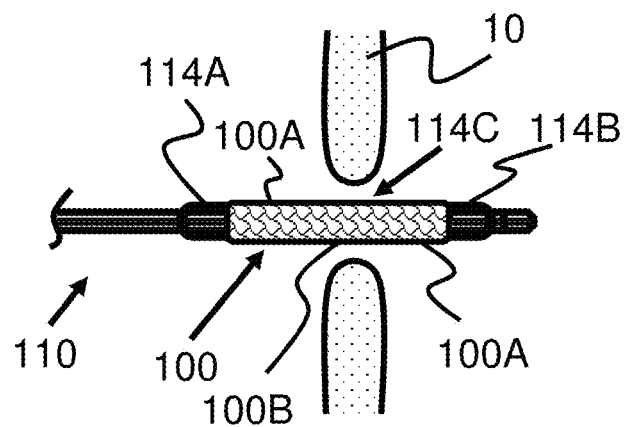
FIG. 9 illustrates a delivery procedure for a shunt according to the present invention.
Figure 10:
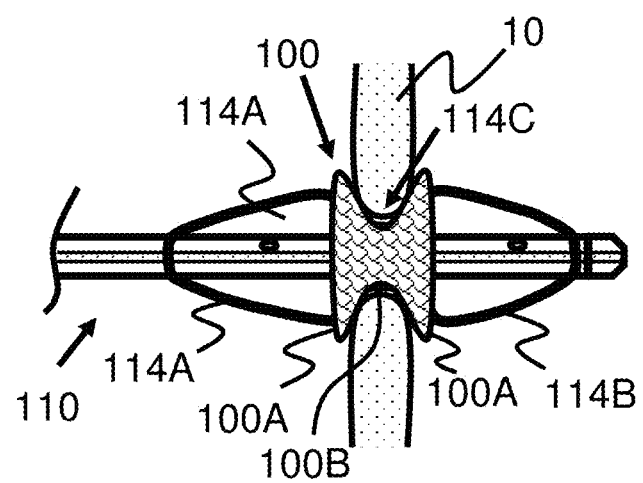
FIG. 10 illustrates a delivery procedure for a shunt according to the present invention.

FIGS. 9 and 10 illustrate how the shunt 100 may be delivered relative to an area of target tissue 10. First, an initial puncture is made at the desired location (e.g., with a needle). Next, the distal end of the delivery catheter 110 is advanced through the puncture in the tissue 10 such that there are roughly equal portions of the shunt 100 on either side of the tissue 10. Either the shunt 100 or the delivery catheter 110 can include radiopaque markers at various known locations to assist a physician with achieving a desired alignment.

When the desired alignment is achieved, the balloon 114 is inflated, causing the shunt 100 to increase in radial diameter to an hourglass shape and to foreshorten. The shunt 100 is configured such that the foreshortening causes the flared end regions 100A to engage and press into the tissue 10. These flared end regions 100A, as well as the proximal region 114A and distal region 114B of the balloon help "self-center" the shunt 100 to an appropriate position. The end result is an opening in the tissue 10 with a smooth, funnel-like transition on each side of the tissue.

One variation on this delivery technique allows for the passage through the shunt 100 (i.e., the narrowed middle region 110B) to be resized after delivery, if needed. Specifically, the shunt 100 can be delivered as previously described, but the narrowed middle region 110B is expanded to an initial diameter that is smaller than the middle region 110B is capable of expanding to. This may be achieved, for example, by limiting the expansion size of the middle region 114C of the balloon 114. If the physician determines that increasing the size of the middle region 100B of the shunt 100 would be beneficial, the middle region 100B can be further expanded in diameter by either a different portion of the balloon (e.g., 114A or 114B) or by a second balloon catheter that inflates to a desired passage diameter.

Alternately, if the physician determines that the middle region 100B of the shunt 100 was initially deployed with a diameter that is larger than desired, a second delivery catheter may be used to deliver a tubular spacer having a thickness that reduces the size of the passage through the middle region 100B. In one example, the tubular spacer may be a second shunt 100, similar to the shunt initially deployed but deployed inside of the first shunt.

This ability to resize the shunt 100 after delivery allows a physician to customize the amount of shunted fluid for each individual patient. It also allows the shunt 100 to be modified at a later date if the patient's hemodynamic needs change.

In an alternate embodiment, the balloon catheter may include two or three separate, independently inflatable balloons that can be inflated to different sizes to achieve a similar hourglass shape. This may allow the physician to limit expansion of the middle of the shunt 100 to a desired diameter while ensuring the ends of the shunt 100 radially expand sufficiently to engage the surrounding tissue.

In another alternate embodiment, a mechanical device on a catheter can be used to expand the shunt 100 instead of using a balloon. For example, such a catheter may include two cone shaped structures that can be longitudinally slid towards each other. The shunt 100 may be positioned between these two structures so that when the cone shaped structures are moved toward each other, they cause the shunt 100 to expand.

Figure 11:
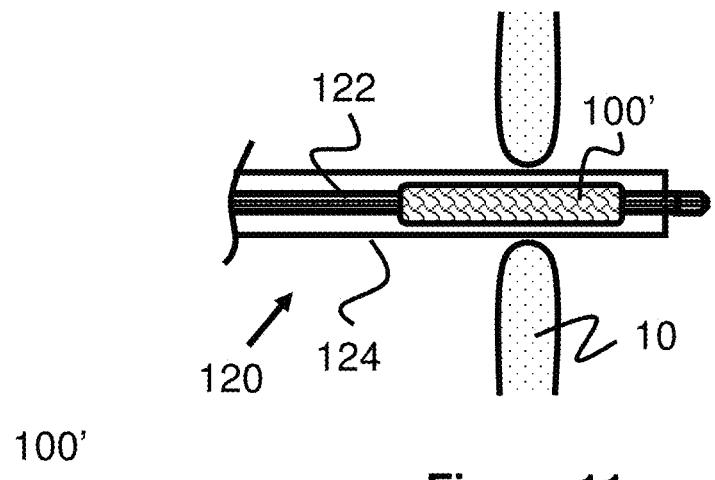
FIG. 11 illustrates a delivery procedure for a shunt according to the present invention.
Figure 12:
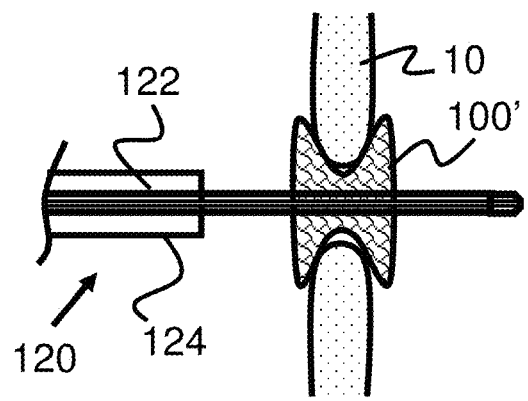
FIG. 12 illustrates a delivery procedure for a shunt according to the present invention.

As previously discussed, the shunt 100' may be composed of a shape-memory material and heat set to the expanded hourglass shape when unconstrained. In such an embodiment, a balloon catheter 110 may not be necessary. FIGS. 11 and 12 illustrate a similar delivery procedure with a delivery catheter 120 configured for deployment of a heat-set shunt 100. The catheter 120 includes an elongated catheter body 122 with a retractable sheath 124 disposed over the shunt 100'. Similar to the previously described deployment procedure, a distal end of the catheter 120 is positioned through the opening in the tissue 10 such that roughly equal portions of the shunt 100 are positioned on each side of the tissue 10. When the desired alignment has been achieved (e.g., by referencing radiopaque markers of a known position), the sheath 124 is proximally retracted, causing the shunt 100' to radially expand to an hourglass shape and foreshorten as shown in FIG. 12.

Figure 13:
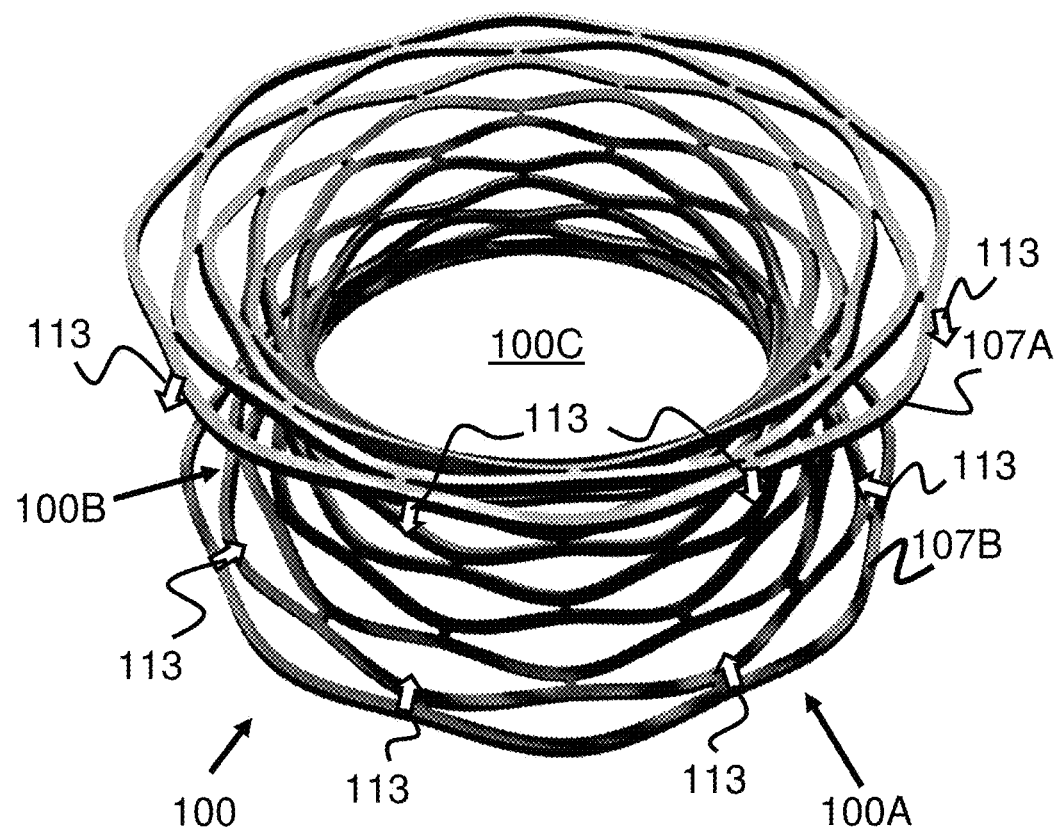
FIG. 13 illustrates a perspective view of another embodiment of a shunt according to the present invention.

In one embodiment, the shunt 100 may include a plurality of barbs 113, hooks, or similar fastening structures, as seen in FIG. 13. These may be positioned on the outside of the flared regions such that they pierce into the tissue of the patient when the shunt 100 is expanded. Alternately, the barbs 113 or similar anchoring structure can be located at various locations along the length of the shunt 100, pointing radially outwards.

In one embodiment, the shunt 100 lacks any type of cover and acts to maintain the opening through the tissue by mechanical force. FIG. 14 illustrates another embodiment of a shunt 130 having a similar laser-cut structure 132 as shunt 100 but also a cover layer 134 that is attached to the laser-cut structure 132 (either on the outside or inside of the structure 132) and forms a similar tubular and hourglass shape. To accommodate the tubular-to-hourglass shape change, part or all of the material 134 may be elastic or stretchable. Alternately, a tubular cover layer 139 can be included only at the middle region of the laser-cut structure 138 of the shunt 136, as seen in FIG. 15.

In another embodiment, either of the shunts may have two laser-cut structural layers that are positioned on the inner and outer surfaces of the cover layer so as to "sandwich" the cover layer.

It is sometimes desirable to occlude an existing shunt (e.g., a naturally occurring tissue passage) or chamber such as a left atrial appendage. In that regard, any of the shunt embodiments in this specification may include a material that extends across and occludes the central lumen of the shunt. For example, the material can be a polymer sheet that is attached to an end of the device with a small hole in the center. The polymer sheet may be elastic so that the enter hole expands with the balloon from the delivery catheter and then recovers back down to effectively seal the opening once the balloon is removed.

Figure 22:
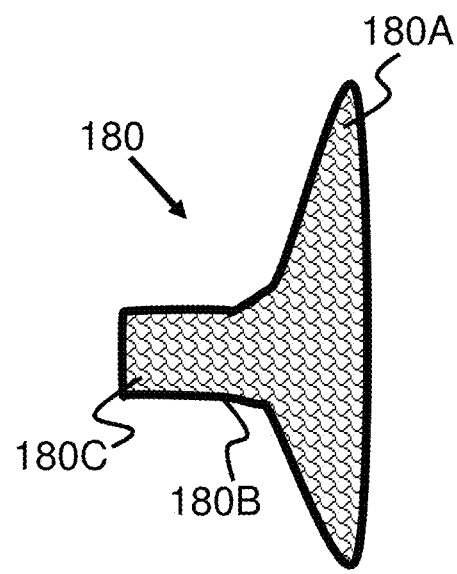
FIG. 22 illustrates a side view of another embodiment of a shunt according to the present invention.

While the shunt 100 and its variations have been previously described to expand to a flared, hourglass style shape, other variations of the expanded shape are possible. For example, FIG. 22 illustrates a shunt 180 in which only one end is radially flared outwards while the opposite end 180C maintains a diameter similar to that of the middle region 180B. Since the shunt 180 foreshortens in length, it may be beneficial to have barbs or other anchoring mechanisms along the middle region 180B and end 180C to help anchor the shunt 180 during radial expansion.

In another example, neither end of the shunt expands to a flared shape.

The shunts of this specification can be composed of biocompatible materials such as Nitinol or similar alloys, or bioabsorbable materials such as magnesium, PLA, or PLA-PGA. The shunts of this specification may also have features to promote endothelization, such as open surface pores around 60 microns in diameter or a polymer coating known to promote tissue growth.

While the shunt 100 was previously described with a specific pattern, it should be appreciated that other patterns and designs are possible to achieve similar functionality. For example, FIGS. 16A and 16B illustrate a shunt 140 comprising a plurality of rings 144 comprising a plurality of alternating peaks. These rings 144 are fixed to a cover 142 and may either be free of connection to each other (other than the cover) or may have connection members 148 that connect to longitudinally adjacent peaks. The ends of the shunt 140 each include end rings 146 that are composed of a plurality of alternating peaks that are larger than those of rings 144. As seen in FIG. 16B, when radially expanded, the peaks 144 longitudinally compress together and fit within each other.

With respect to FIG. 16B, in one embodiment, the shape depicted therein may be achieved by over-expanding the shunt by a balloon, which would cause the ends to flare open as shown and the central section expansion would be limited by the cover 142.

Figure 17:
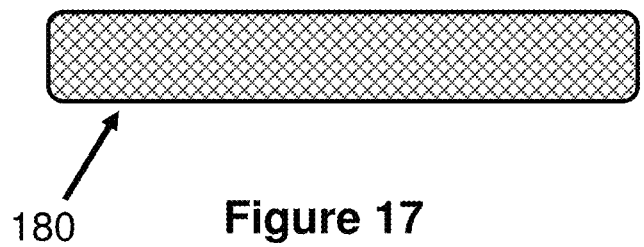
FIG. 17 illustrates a side view of another embodiment of a shunt according to the present invention.
Figure 18:
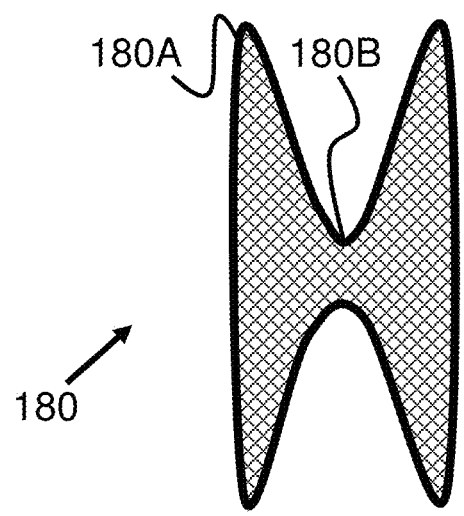
FIG. 18 illustrates a side view of the shunt of FIG. 17.

In addition to having different laser-cut patterns, alternate embodiments may instead be comprised of a plurality of braided wires, such as the shunt 180 shown in FIGS. 17 and 18. The shunt 180 can be braided on an hourglass-shaped mandrel with a plurality of shape-memory wires. After braiding, the shunt 180 can be heat-set on the mandrel and then removed, allowing it to compress to a tubular shape and radially expand to the hourglass shape (i.e., flared end regions 180A and a smaller diameter middle region 180B).

As previously discussed, the delivery catheters 110 and 120 can include radiopaque markers to help a physician align the shunt 100. However, other positioning devices can also be used to aid in positioning.

Figure 19:
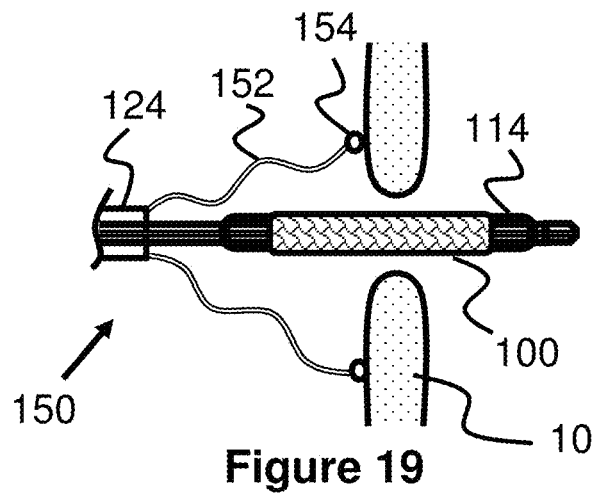
FIG. 19 illustrates an alternate embodiment of a balloon catheter according to the present invention.

For example, FIG. 19 illustrates a delivery device 150 that includes elongated arms 152 that are connected to the catheter body at their proximal ends and are configured to radially expand away from the shunt 100 at their distal ends 154. The arms 152 are preferably of a length that the blunt distal ends contact the tissue 10 when the shunt 100 is positioned at a desired alignment position (e.g., roughly halfway through the opening). This contact by the arms 152 provides the user with tactile feedback in addition to the visualization of the radiopaque markers. To prevent damage to the tissue 10, the arms 152 are preferably composed of flexible material, such as nitinol, stainless steel, polyether block amide (also known by the tradename Pebax®), nylon, polyurethane, or other plastics. The arms 152 can be relatively straight or can form a plurality of waves to provide further flexibility and compression.

Figure 20:
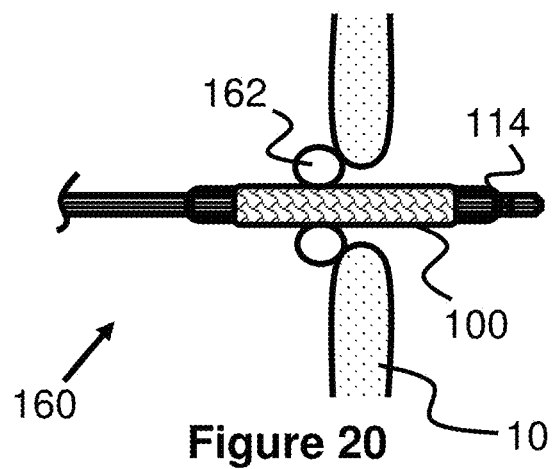
FIG. 20 illustrates an alternate embodiment of a balloon catheter according to the present invention.

FIG. 20 illustrates another embodiment of a delivery device 160 that includes an annular ring 162 located over the shunt 100 to assist with a desired alignment of the shunt 100. The annular ring 162 preferably has a thickness such that it is larger than the opening of the tissue 10 when the shunt 100 is compressed. The ring 162 is longitudinally positioned on a proximal side of the shunt 100 such that when contact is made between the ring 162 and tissue 10, the shunt 100 will have achieved a desired longitudinal alignment through the tissue opening. The ring 162 can be composed of cloth, polymer, or bioabsorbable material.

Figure 21:
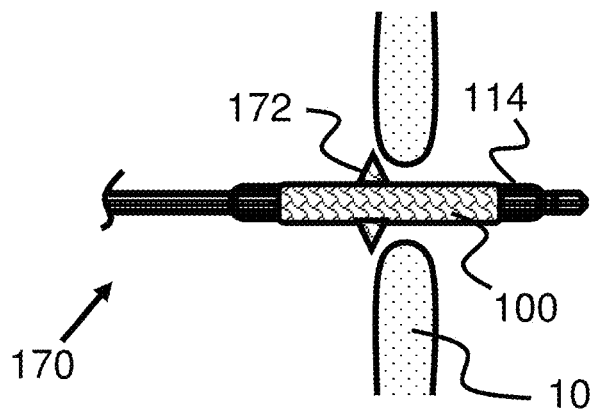
FIG. 21 illustrates an alternate embodiment of a balloon catheter according to the present invention.

Alternately, instead of an annular ring 162, the shunt 100 itself may include structures 172 on the shunt 100 that are heat-set to radially expand, as seen on device 170 in FIG. 21. For example, the structures may be a loop, flap, or similar structure that radially pops up when an overlying sheath is withdrawn from the shunt. Similar to the ring 162, these structures 172 are positioned at a location so as to provide tactile feedback to the physician to indicate a desired alignment of the shunt 100 within the tissue opening.

While the specification has focused on various embodiments of a shunt that are used for creating a shunt within a patient or closing a hole between two vessels or heart chambers, other uses are also possible. For example, the shunt 100 may be used an anchor and/or attachment point for additional structures (e.g., tubes, other shunts, etc.). In another example, the shunt 100 may be used as an anchoring point for artificial valves, such as a mitral valve or aortic valve. In another example, the shunt 100 may be used to help restore a circular shape to a structure (e.g., aortic coarctation).

The shunts and delivery methods described in this specification can be used for a wide variety of shunt procedures. One example is a right-to-right shunt between the right pulmonary artery to superior vena cave, between the pulmonary artery to right atrial appendage, between the pulmonary artery or right ventricle to the venous system, or between the azygous vein to the inferior vena cava. These techniques can be seen in more detail in application Ser. No. 16/576,704 entitled Methods And Technology For Creating Connections And Shunts Between Vessels And Chambers Of Biologic Structures, filed Sep. 19, 2019 which is herein incorporated by reference. Other possible uses include the creation of shunts between chambers of the heart, such as atrial septostomy, arteriovenous shunt creation for treating hypertension, arteriovenous shunt for fistula creation for dialysis patients, left atrium to coronary sinus, pulmonary artery to left aortic artery, or aorta to pulmonary artery.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A prosthesis system for creating a shunt, comprising:
    a tubular structure having a radially compressed configuration and a radially expanded configuration;
    the tubular structure comprising a laser-cut pattern comprising a plurality of cells that progressively increase in cell sizes from a middle of the tubular structure to axially located end regions of the tubular structure;
    wherein the radially expanded configuration of the tubular structure foreshortens in axial length during expansion from the radially compressed configuration to an amount determined by the progressively increasing cell sizes of the laser-cut pattern;
    wherein the radially expanded configuration of the tubular structure radially flares axially located end regions to a shape determined by the progressively increasing cell sizes of the laser-cut pattern; and,
    a balloon positioned under the tubular structure.

2. The prosthesis system of claim 1, wherein the tubular structure foreshortens in axial length during expansion of the tubular structure an amount such that the axially located end regions press and engage tissue of two biological lumens positioned therebetween.

3. The prosthesis system of claim 1, wherein the tubular structure has a radially compressed length of about 30 mm and a radially compressed diameter of about 2.2 mm.

4. The prosthesis system of claim 1, wherein the axially located end regions of the tubular structure have diameters of about 8 mm, and the middle of the tubular structure has a radially expanded diameter of about 4 mm.

5. The prosthesis system of claim 1, wherein in the radially expanded configuration the tubular structure is configured to form a smooth, funnel-like shunt passage between a first body lumen and a second body lumen.

6. The prosthesis system of claim 1, wherein the balloon has an inflated shape of an hourglass when inflated underneath the tubular structure.

7. The prosthesis system of claim 1, wherein the plurality of cells are diamond-shaped cells.

8. The prosthesis system of claim 1, wherein the tubular structure is heat-set to an hourglass shape.

9. The prosthesis system of claim 1, wherein the balloon is located on a catheter, and wherein the catheter further comprises a positioning device configured to position the tubular structure, the positioning device comprising elongated arms that expand radially outward from the catheter, an annular ring, or radially expandable loops.

10. A prosthesis system for creating a shunt, comprising:
    a tubular structure having a radially compressed configuration and a radially expanded configuration; the tubular structure comprising a laser-cut pattern comprising a plurality of cells that progressively increase in cell sizes from a middle of the tubular structure to axially located end regions of the tubular structure; wherein the radially expanded configuration of the tubular structure foreshortens in axial length during expansion from the radially compressed configuration to an amount determined by the progressively increasing cell sizes of the laser-cut pattern; wherein the radially expanded configuration of the tubular structure radially flares axially located end regions to a shape determined by the progressively increasing cell sizes of the laser-cut pattern.

11. The prosthesis system of claim 10, further comprising a balloon catheter having a balloon; wherein the tubular structure is disposed over the balloon.

12. The prosthesis system of claim 11, wherein the balloon has an inflated shape of an hourglass when inflated underneath the tubular structure.

13. The prosthesis system of claim 11, wherein the catheter further comprises a positioning device configured to position the tubular structure, the positioning device comprising elongated arms that expand radially outward from the catheter, an annular ring, or radially expandable loops.

14. The prosthesis system of claim 10, wherein the tubular structure foreshortens in axial length during expansion of the tubular structure an amount such that the axially located end regions press and engage tissue of two biological lumens positioned therebetween.

15. The prosthesis system of claim 10, wherein in the radially expanded configuration the tubular structure is configured to form a smooth, funnel-like shunt passage between a first body lumen and a second body lumen.

16. The prosthesis system of claim 10, wherein the plurality of cells comprise diamond-shaped cells.

17. The prosthesis system of claim 10, wherein the tubular structure is heat-set to an hourglass shape.

18. A prosthesis system for creating a shunt, comprising:
    a tubular stent-like structure having a radially compressed configuration and a radially expanded configuration; the tubular stent-like structure comprising a laser-cut pattern comprising a plurality of cells that progressively increase in cell sizes from a middle of the tubular structure to axially located end regions of the tubular structure; wherein the radially expanded configuration of the tubular structure foreshortens in axial length during expansion from the radially compressed configuration to an amount determined by the progressively increasing cell sizes of the laser-cut pattern; wherein the radially expanded configuration of the tubular structure radially flares proximal and distal end regions to a shape determined by the progressively increasing cell sizes of the laser-cut pattern.

19. The prosthesis system of claim 18, wherein in the radially expanded configuration the tubular stent-like structure forms a smooth, funnel-like shunt passage between a first body lumen and a second body lumen.

* * * * *